United States Patent [19]

Kohayakawa et al.

[11] Patent Number: 5,037,194

[45] Date of Patent: Aug. 6, 1991

[54] OPHTHALMOLOGIC APPARATUS AND METHOD OF COMPOUNDING THE IMAGE OF AN EYE TO BE EXAMINED

[75] Inventors: Yoshimi Kohayakawa, Yokohama; Kenichi Kashiwagi, Kawasaki; Isao Matsumura, Yokosuka, all of Japan

[73] Assignee: Canon Kabushiki Kaisha, Tokyo, Japan

[21] Appl. No.: 360,135

[22] Filed: May 31, 1989

[30] Foreign Application Priority Data

| May 31, 1988 | [JP] | Japan | 63-133147 |
| May 31, 1988 | [JP] | Japan | 63-133150 |
| Aug. 12, 1988 | [JP] | Japan | 63-201178 |
| Mar. 30, 1989 | [JP] | Japan | 1-80881 |

[51] Int. Cl.$^5$ .................................................. A61B 3/02
[52] U.S. Cl. .................................... 351/224; 351/206; 351/212

[58] Field of Search ................ 351/206, 211, 214, 212, 351/224, 226, 221

[56] References Cited

U.S. PATENT DOCUMENTS

4,279,478 7/1981 Matsumura .......................... 351/224

Primary Examiner—Paul M. Dzierzynski
Attorney, Agent, or Firm—Fitzpatrick, Cella, Harper & Scinto

[57] ABSTRACT

An ophthalmologic apparatus characterized by the provision of a device for introducing thereinto an eye fundus image at a point in time earlier than the point in time of view field measurment, a device for measuring the field of view of an eye to be examined, and a device for superposing the introduced eye fundus image and the output of the view field measuring a device, one upon the other, and compounding them.

41 Claims, 5 Drawing Sheets

OPHTHALMOLOGIC APPARATUS AND METHOD OF COMPOUNDING THE IMAGE OF AN EYE TO BE EXAMINED

BACKGROUND OF THE INVENTION

1. Field of the Invention

This invention relates to an ophthalmologic apparatus which can compound the result of the measurement of the field of view of an eye to be examined and relates a corresponding eye fundus image, and to a method of compounding the image of the eye to be examined.

2. Related Background Art

Figure 11:
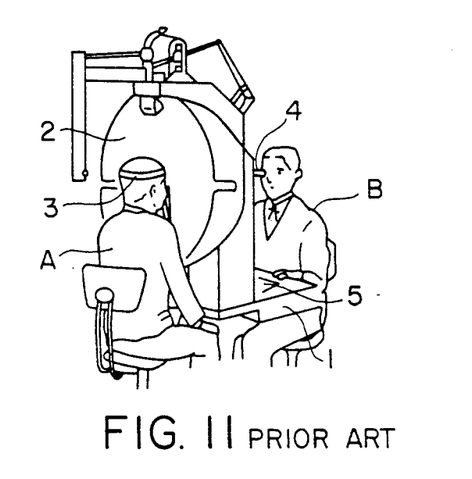
FIG. 11 shows the whole of a perimeter according to the prior art.
Figure 12:
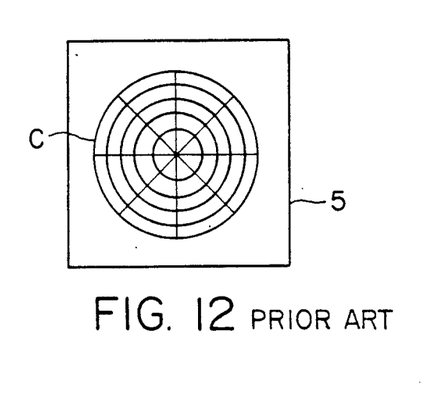
FIG. 12 shows an example of the format of the view field chart.

Perimeters have heretofore been widely used to measure the fields of view of examinees. The outline of such perimeters will hereinafter be described with reference to FIG. 11 of the accompanying drawings. FIG. 11 illustrates a perimeter and its measuring state. The perimeter is fixedly constructed on a table 1 so that the inner surface of a substantially hemispherical dome 2 faces an examinee A and the outer surface of the dome 2 faces an examiner B. The examinee A has his face fixed by a fixing member 3 provided on the inner surface of the dome. The examinee A responds as to whether he could recognize an index presented successively on the inner surface while watching a fixation target on the inner surface of the dome 2. The examiner presents an index on the inner surface of the dome 2 while monitoring the gazing point of the examinee A by means of a loupe 4 provided on the outer surface side of the dome 2, and manually records the result of the response on recording paper 5 disposed on the table 1. FIG. 12 shows an example of the format of a view field chart on the recording paper 5, and the result of the response is plotted by the help of the view field chart printed on the recording paper 5, for example, the view field chart C comprising a plurality of concentric circles and four axes in directions to divide these concentric circles into eight parts. Besides this method, use has been made of a method using a TV monitor, instead of the recording paper 5, to plot measuring points on a view field chart on the TV monitor.

Heretofore, when determining the correspondence between this output result and the fundus of the eye to be examined, the examiner had to compare the photograph of the eye fundus with view field data with his eyes on the basis of the information of the center of the field of view and the blind spot portion of the field of view this was inefficient.

On the other hand, there is also known an eye fundus perimeter in which the view field measuring function is added to the eye fundus photographing function and a photographing output having the result of view field measurement imprinted on an eye fundus image is obtained. This perimeter is such that infrared light is applied to an eye to be examined and the examiner moves the index of visible light while observing the infrared eye fundus image of the eye fundus image on a TV monitor, and plots by means of a pen on a light-transmitting recording plate mounted in the apparatus or plots by perforating recording paper, in accordance with the examinee's response, and the plot image, together with the infrared eye fundus image, is displayed on the TV monitor and simultaneously with the photographing of the fundus of the eye, a final plot image is imprinted on the photograph. This is described in detail, for example, in U.S. Pat. No. 4,279,478.

However, in this prior-art eye fundus perimeter, the eye fundus image capable of being displayed is only the eye fundus image in real time during the view field measurement, and the past eye fundus images or the like cannot be displayed. That is, for example, even if there is a desire to measure the field of view while observing the eye fundus image before a disease has been cured, it is impossible with such a the prior-art type device.

Also, the eye fundus image produced by infrared light is not clear and further, infrared light penetrates more deeply into the interior of the fundus of the eye than visible light and therefore, the resultant infrared image is an image of the deeper portion of the fundus than the visible image, and this has led to the problem that such image differs from the outermost eye fundus image.

Also, during long-time view field measurement, it has been necessary to apply infrared light to an eye to be examined.

SUMMARY OF THE INVENTION

It is an object of the present invention to provide an ophthalmologic apparatus which can obtain a compound image of view field data and a corresponding eye fundus image at any point in time differing from the point in time of view field measurement.

It is another object of the present invention to provide an ophthalmologic apparatus by which view field measurement is possible while the examiner is watching an eye fundus image at any point in time differing from the point in time the view field measurement (for example, an eye fundus image in the past before a disease of the eye has been cured).

It is still another object of the present invention to provide an ophthalmologic apparatus by which view field measurement is possible while the examiner is watching an eye fundus photograph image by visible light.

It is yet still another object of the present invention to provide an ophthalmologic apparatus by which view field measurement is possible without the use of infrared light while the examiner is watching a corresponding eye fundus image.

It is a further object of the present invention to provide an ophthalmologic apparatus by which view field measurement is possible while the examiner is watching a clear-cut corresponding eye fundus image.

It is still a further object of the present invention to provide an ophthalmologic apparatus which can obtain a compound image of a distortion-free eye fundus image of an eye to be examined and corresponding view field data.

It is yet still a further object of the present invention to provide an ophthalmologic apparatus which can obtain a compound image of a wide angle of view.

DESCRIPTION OF THE PREFERRED EMBODIMENTS (Embodiment 1)

Figure 1:
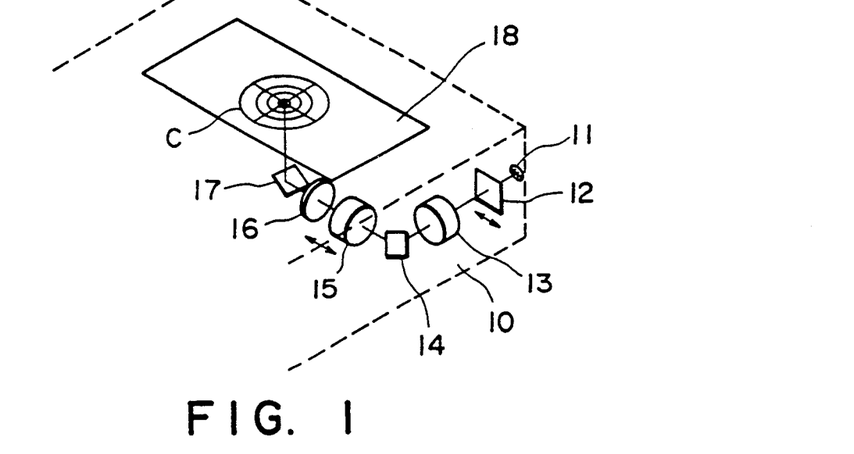
FIG. 1 shows the construction of a first embodiment of the present invention.

FIG. 1 shows the construction of a first embodiment of the present invention, and more particularly shows the perspective construction of the recording table 10 of a view field meter. Incorporated in the table 10 is an optical system for projecting onto recording paper an eye fundus image photographed by the use of light from a photographing light source which emits visible light. This optical system comprises, in succession from the light source 11, a removably mounted slide film 12 upon which the eye fundus image falls, a relay lens 13, a reflecting mirror 14, a magnification changing lens 15, a projection lens 16 and a reflecting mirror 17 disposed in the optical path. The table 10 has an upper portion thereof formed of a light-transmitting member such as a glass plate, and recording paper 18 is interchangeably placed on that portion.

The slide film 12 on which the eye fundus image of an eye to be examined has been photographed in advance is illuminated by the light source 11. This light enters the magnification changing lens 15 via the relay lens 13 and the reflecting mirror 14. The eye fundus image on the slide film 12 is not limited to an image photographed by an ordinary eye fundus camera, but may also be an image which has been distortion-corrected or an eye fundus image of a wide angle of view, as will be described later with respect to Embodiment 4. The slide film 12 is finely movable in vertical and horizontal directions, and alignment is effected so that the projected eye fundus image may coincide with a view field chart C printed on the recording paper 18. The magnification changing lens 15 has its focal length freely variable from the exterior, and is adjusted so as to form an eye fundus image of an appropriate size on the recording paper 18 on the table 10. The light which has left the magnification changing lens 15 projects, via the projection lens 16 and the reflecting mirror 17, the eye fundus image from the back surface of the recording paper 18 having a light-transmitting type screen characteristic.

Since the view field chart C is printed on the recording paper 18, there is obtained a compound image in which the projected eye fundus image and the field chart C overlap each other. The recording paper 18 is freely replaceable and can always be set at the same position if it is in accord with a predetermined format. Even when use is made of recording paper of another different format, it can be freely changed in its position so as to be aligned with the eye fundus image. Usually, the recording paper is disposed so as to correspond to the index presentation position of a view field measuring device in a 1:1 correspondence and therefore, it need not always have a chart printed thereon, and the result view field measurement may be plotted on only the projected eye fundus image.

To make the projected eye fundus image coincident with the view field chart, the slide film 12 and the magnification changing lens 15 are adjusted. As regards alignment, the slide film 12 is moved in vertical and horizontal directions to bring the view field center of the view field chart into coincidence with the yellow spot of the eye fundus image. When there is a deviation between the blind spot of the view field chart found in the course of measurement and the optic disk of the eye fundus image, they are brought into coincidence with each other as required. Also, as regards the adjustment of magnification, the inverse number of the photographing magnification of the eye fundus image recorded on the slide film 12 is set as the projection magnification.

Figures 2, 3:
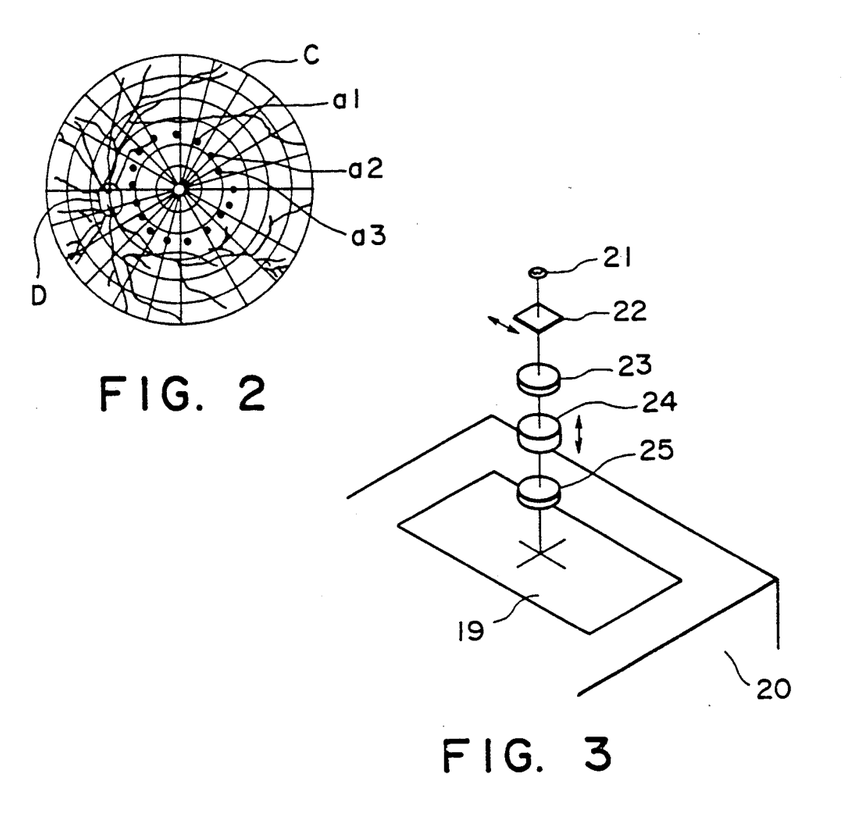
FIG. 2 shows an example of the output of the first embodiment.
FIG. 3 shows the construction of a second embodiment of the present invention.

FIG. 2 shows an example of a state in which the result of measurement is being recorded. The view field chart C comprising a plurality of concentric circles and radial straight lines equally dividing these concentric circles and the projected eye fundus image D are compoundly displayed in superposed relationship with each other on the recording paper 18 placed on the table 10 in front of the examiner. The result of the measurement of the view field is successively recorded as plots al-an on the recording paper 18 by the examiner or is automatically recorded by a machine.

(Embodiment 2)

FIG. 3 shows the construction of a second embodiment of the present invention which is a modified form of the above-described embodiment. An opaque material is used as recording paper 19, and an eye fundus image may be projected from above the recording paper 19. A light source 21 is installed above the recording paper 19 placed on a table 20, and a slide film 22, a relay lens 23, a magnification changing lens 24 and a projection lens 25 are disposed in succession on the optical path from the light source 21 toward the table 20. The slide film 22 is finely movable for alignment. These constituents have the same action as the previous embodiment, that is, an eye fundus image can be formed on the recording paper and the eye fundus image can be superposed on the view field chart C on the recording paper 19.

In the constructions of the present and previous embodiments, it is also possible to use the apparatus in such a manner that the view field chart measured and recorded by an ordinary view field meter is mounted on the apparatus of the present or previous embodiment and the examiner makes a diagnosis while watching the compound image of the view field chart and the eye fundus image.

(Embodiment 3)

Figure 4:
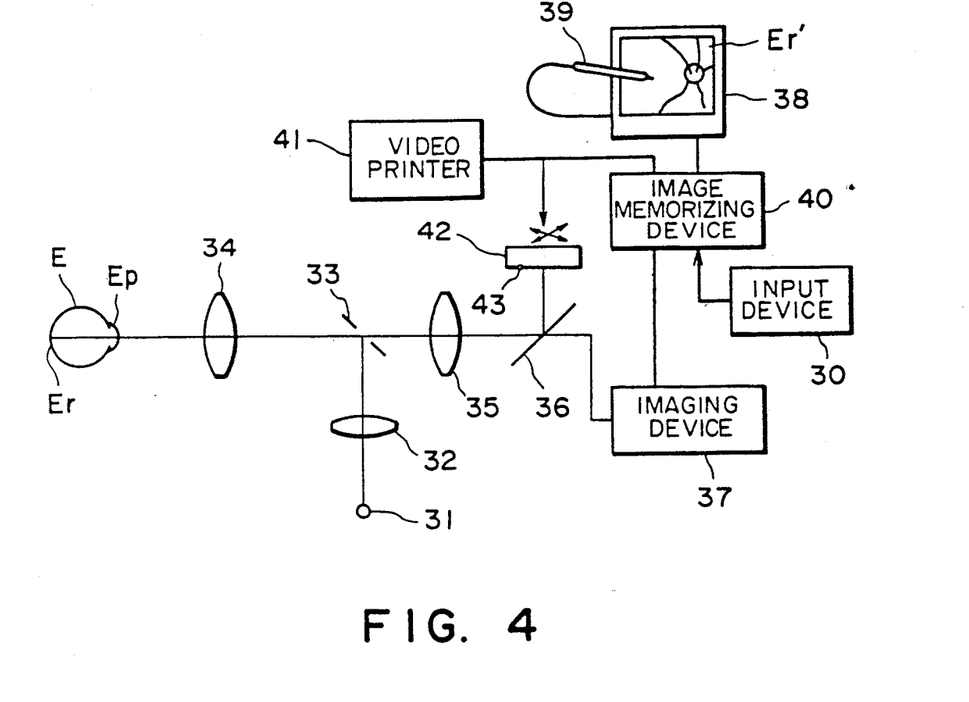
FIG. 4 shows the construction of a third embodiment of the present invention.

Referring to FIG. 4 which shows a third embodiment of the present invention. An illuminating system lens 32, an apertured mirror 33 and an objective lens 34 are arranged in succession on an optical path passing through a photographing light source 31 which is an eye fundus photographing means and an eye E to be examined. The apertured mirror 33 is made conjugate with the pupil Ep of the eye E to be examined by the objective lens 34. An imaging lens 35, a beam splitter member 36 and an image pickup device 37 are arranged in succession rearwardly of the apertured mirror 33 so that the eye fundus image may be formed on the image pickup element of the image pickup device 37. The image pickup element may preferably be an area sensor array such as a CCD which will not engender distortion. The output of the image pickup device 37 is connected to an image memorizing device 40, to which is also connected an input device 30 for inputting an eye fundus image from the exterior. The output of the image memorizing device 40 is connected to a display device 38 such as a liquid crystal TV, and a light pen 39 is connected to the display device 38. The output of the image memorizing device 40 is also connected to a video printer 41 and a stimulative light source driving device 42. The stimulative light source driving device 42 is a moving means for a stimulative light source 43, and a light beam from the stimulative light source 43 is adapted to be directed into the optical path to the eye fundus Er through the beam splitter member 36.

In the construction described above, the fundus of the eye to be examined is first photographed before the field of view is measured. During the photographing of the eye fundus, the photographing light source 31 flashes and emits a visible light, which illuminating system lens 32, the apertured mirror 33, the objective lens 34 and the pupil Ep. The eye fundus image is formed on the image pickup element of the image pickup device 37 via the pupil Ep, the objective lens 34, the apertured mirror 33, the imaging lens 35 and the beam splitter member 36 and is memorized in the image memorizing device 40. The image memorizing device 40 memorizes a stationary video signal or digital signals. The content of the image memorizing device 40 is displayed as a stationary eye fundus image Er' on the display device 38.

Figure 10:
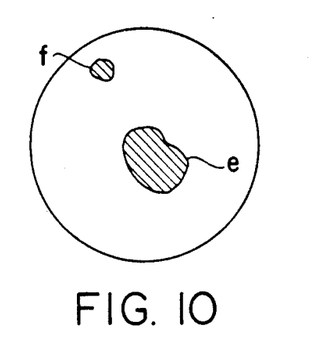
FIG. 10 shows an example of an eye fundus image having a morbid part.

If desired, photographing of the eye fundus may not be effected by the apparatus of the present embodiment, but the eye fundus image photographed by a discrete eye fundus photographing apparatus may be input from the photographing angle of view, i.e., the magnification, and may be memorized by the image memorizing device 40 and displayed on the display device 38. By doing so, it also becomes possible to accomplish the measurement of the field of view chiefly about a morbid part while watching the past eye fundus image in which, as shown, for example, in FIG. 10, the morbid part (e designates a bleeding spot, and f denotes a white spot) was photographed.

The examiner carries out the measurement of the field of view while watching the stationary eye fundus image being thus displayed, and when the examiner designates a desired view field measuring point on the eye fundus screen of the display device 38 by means of the light pen 39, the stimulative light source driving device 42 moves the stimulative light source 43 in conformity with the coordinates on the screen read by the light pen, i.e., the designated position of the eye fundus image, and a stimulative light is emitted toward the designated measuring point of the eye fundus Er. A stimulating method is, for example, static perimeter. This method is such that the luminance of the stimulative light is visually unrecognizably weak at the beginning and is gradually intensified and at a point of time whereat the examinee visually recognizes the stimulative light, the examinee responds by means of a switch or the like and the then luminance of the stimulative light and the then position of the measuring point are introduced as a measured value and memorized. At this time, view field measurement data are image-compounded and displayed on the display device 38. Various display methods such as displaying a point of a color conforming to the luminance of the stimulative light, and changing the size of the point in conformity with the luminance or the size of the index are within contemplation. In this manner, measurement of numerous positions is progressed, and the final result of the measurement is output to the video printer 41 on the basis of the content of the image memorizing device 40. Without the view field measurement data being displayed on the display device 38, the compound result may be output only to the video printer 41.

Figure 5:
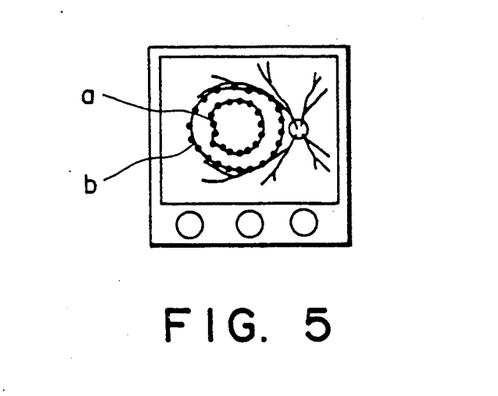
FIG. 5 shows an example of the output of the third embodiment.

FIG. 5 shows an example of the output, and curves a and b are isopters prepared by linking respective measuring points together. These isopters, if classified by color, will become easy to see.

The means for designating the measuring point is not limited to the light pen, but may be one of various well-known input means, and for example, the index may be moved by the use of input means such as a mouth, a track ball, a digitizer, a touch panel or a keyboard.

(Embodiment 4)

Figure 6:
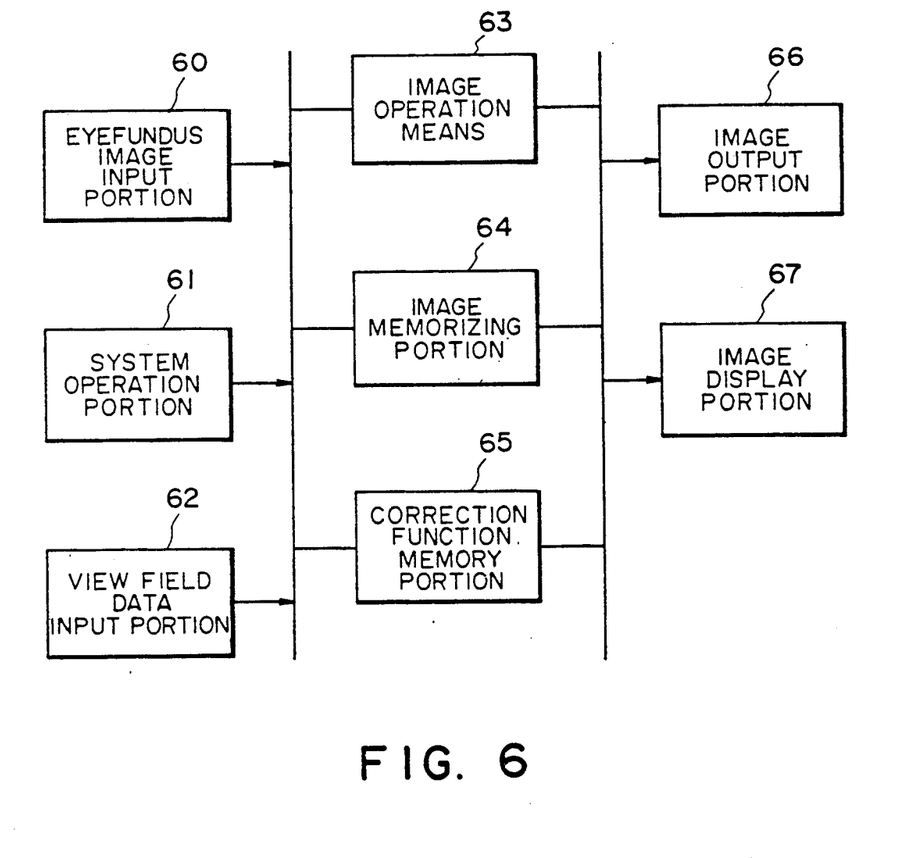
FIG. 6 shows the construction of a fourth embodiment of the present invention.

FIG. 6 shows the construction of portions for compounding the eye fundus image and view field measurement data, as a fourth embodiment of the present invention, and in this figure, the perimeter and the transfer of the data obtained from the perimeter are omitted. In FIG. 6, the reference numeral 60 designates an eye fundus image input portion for reading and inputting an image in which the eye fundus image of the eye to be examined is recorded, which eye fundus image input portion may, for example, be a 35 mm slide scanner for reading a 35 mm slide and inputting the eye fundus image. The reference numeral 61 denotes a system operation portion for the operator to input a command to the system, the reference numeral 62 designates a view field data input portion for inputting the output signal of view field measuring means which measures the field of view of the eye to be examined, the reference numeral 63 denotes an image operation means for carrying out numerous operations such as image processing and control of the system, the reference numeral 64 designates an image memorizing portion for memorizing the image, the reference numeral 65 denotes a correction function memory portion for memorizing the correction function of the distortions of various eye fundus cameras, and the reference numeral 66 designates an image output portion such as a printer for outputting the compound image of the corrected eye fundus image and the view field data. This image output portion 66 print-outputs the compound image in a color or colors. The reference numeral 67 denotes an image display portion such as a TV monitor for displaying the memorized image in the image memorizing portion 64.

A specific method of carrying out the present embodiment will now be described in detail. First, the eye fundus image recorded on a 35 mm slide prepared in advance is read and input from the image input portion 60, and thereafter is A/D converted and digitally stored into the image memorizing portion 64. In the present embodiment, an example of the 35 mm slide scanner is shown, whereas this is not restrictive, but the image input portion may be, for example, an eye fundus photographing means such as an eye fundus camera having an A/D converting interface, or a means which can provide an eye fundus image, such as a still video camera.

Figure 7:
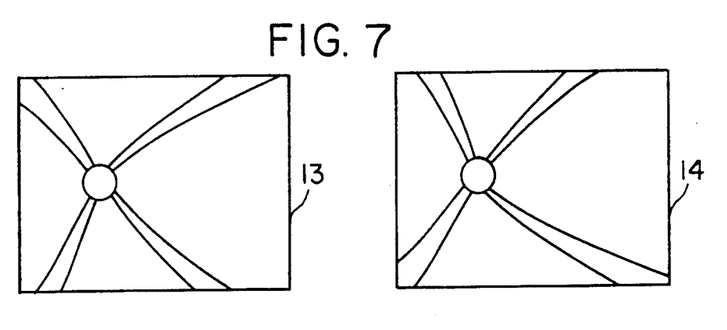
FIG. 7 illustrates the correction of the distortion of an eye fundus image.

Generally an image photographed by an eye fundus camera or the like has distortion in the marginal portion thereof. So, the distortion of the marginal portion of the input image memorized in the image memorizing portion 64 is digitally corrected as indicated by 13 to 14 in FIG. 7, by the use of the distortion correction function memorized in the correction function memory portion 65, and the corrected image is again stored into the image memorizing portion 64. As a specific example of the method correcting the distortion of the marginal portion of the image, the image is displaced by $\Delta\gamma$ calculated from the correction function in each meridian direction from the center of the image. More particularly, each optic axis height, i.e., the displacement $\Delta\gamma$ in the meridian direction caused by distortion correspondingly to the position of a radius $\gamma$ from the center of the image, is measured or calculated in advance, and these are received as distortion data into a memory, and during data processing, the position information of the digital image signal is corrected by an amount corresponding to the displacement $\Delta\gamma$.

Figure 8:
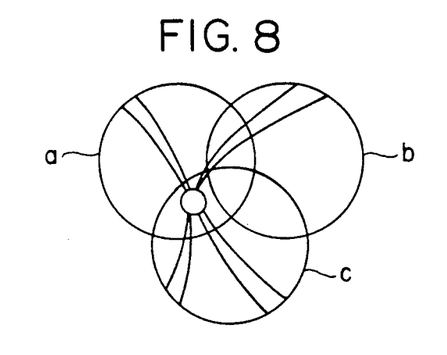
FIG. 8 illustrates the making of a panorama eye fundus image.

The eye fundus image used in the present embodiment is not limited to a photographed image of a narrow angle of view which can be photographed at one time, but may also be a distortion-free panorama eye fundus image of a wide angle of view obtained by combining a plurality of eye fundus images obtained by photographing different regions, as shown in FIG. 8. Nowadays, the angle of view covered by an eye fundus camera at one time is generally of the order of 30°-60°, but this problem can be solved by using a panorama eye fundus image. In this case, a plurality of images are input from the eye fundus image input portion 60 and memorized in the image memorizing portion 64, and correction of distortion and combinating of the images are effected in the image operation means. If correction of distortion is effected before the eye fundus images a, b and c are combined together as shown in FIG. 8, there will occur no deviation of the images due to distortion in the connected portions of the images. The combining of the images can be manually or automatically accomplished from the pattern of blood vessels or the like by the use of a conventional image recognition processing technique.

Thus, the image subjected to distortion correction for the input eye fundus image, or the panorama eye fundus image obtained by combining the plurality of images of displayed on the image display portion 67. The examiner carried out the measurement of the field of view while watching this displayed eye fundus image, and a specific method of compounding the eye fundus image and the view field data will hereinafter be described.

As regards the view field data successively sent from the view field measuring means during the measurement of the field of view, the data are recorded at a corresponding position on the eye fundus image memorized in the image memorizing portion, and are displayed on the image display portion 67 successively, individually or in a postscript fashion. Alternatively, the eye fundus image and all view field data may be compounded at a time after the completion of the measurement.

Figure 9:
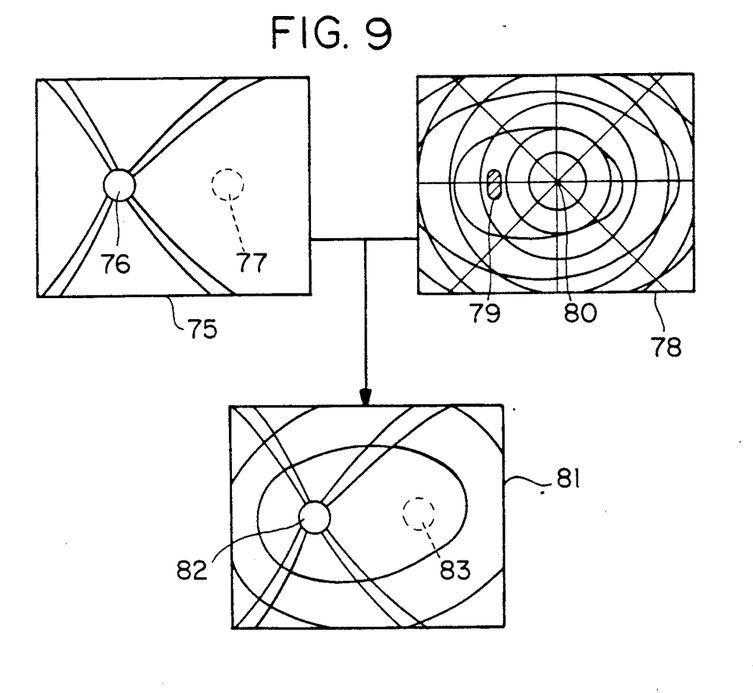
FIG. 9 illustrates the compounding of an eye fundus image and a view field chart.

In FIG. 9, the reference numeral 75 designates the eye fundus image after the distortion of the eye fundus camera has been corrected, the reference numeral 76 denotes the optic disk, and the reference numeral 77 designates a yellow spot. The reference numeral 78 denotes the view field data of the eye to be examined corresponding to the eye fundus image 75, the reference numeral 79 designates the blind spot, and the reference numeral 80 denotes the center of fixation. Here, in the eye fundus image 75 and the image of the view field data 78, the optic disk 76 and the blind spot 79, and the yellow spot 77 and the center of fixation 80, correspond to each other as the same regions. In the image operation means 63, these two points are extracted from the two images by the use of the image recognition processing technique, and the process of adjusting the two images so as to bring the two points into coincidence with each other and superposing the two images one upon the other is carried out.

During the superposition, the eye fundus image 75 and the view field data 78 are in mirror image relationship and therefore, the mirror image inverting process of the view field data 78 is first effected and then the compounding of the images is effected. The mirror image inverting process can be easily accomplished because the view field data 78 is digital data.

When the eye fundus image 75 and the image of the view field data 78 differ in scale and the two points cannot be brought into coincidence with each other at the same time, one of the two images is enlarged or reduced to make the sizes of the two images equal to each other. In the example shown in FIG. 9, the view field data 78 is enlarged. As an example of the processing method in this case, the distance between the optic disk and the yellow spot in the eye fundus image and the distance between the blind spot and the center of the field of view in the view field meter output image are measured, and the total sizes of one or both images are changed so that these two distances may correspond with each other. After the sizes of the both images have corresponded with each other, the respective points are brought into coincidence with each other and the both images are adjusted and compounded. As an alternative method, the centers of the fields of view of the both images and an image of a predetermined angle of view (e.g. 60°) centered at the yellow spot may be extracted and these extracted images may be magnification-changed and compounded so that they may coincide with each other. During the enlargement, it will be more preferable to carry out a picture element interpolation process. Thus, there can be obtained a compound image 81 as shown in the lower portion of FIG. 9 wherein the optic disk and the blind spot coincide with each other at 82 and the yellow spot and the center of the field of view coincide with each other at 83.

As the view field data display method, besides the display method using the isopters of the embodiment, various forms of display such as density display and display by color are possible.

We claim:

1. An ophthalmologic image compound apparatus, comprising:
    first input means for introducing an eye fundus image photographed previous to a view field measurement;
    second input means for introducing data of the view field of an eye to be examined by means of a view field measuring means;
    correction means for correcting at least one of said eye fundus image and said view field measuring data so that said eye fundus image and the view field measuring data are in a one-to-one correspondence with each other; and
    compound means for compounding corrected eye fundus image and view field measuring data corrected by said correction means.

2. An ophthalmologic image compound apparatus according to claim 1, wherein:
    said correction means includes means for correcting at least one of magnification and distortion.

3. An ophthalmologic image compound apparatus according to claim 1, wherein:

said compound means includes an optical system for optically compounding said data.

4. An ophthalmologic image compound apparatus according to claim 1, wherein:
said compound means includes a compound circuit for electrically compounding said data.

5. An ophthalmologic image compound apparatus according to claim 1, wherein:
said eye fundus image is a visible eye fundus image photographed under the application of visible light.

6. An ophthalmologic image compound method, comprising:
an eye fundus image input step for introducing an eye fundus image photographed previous to a view field measurement into an apparatus;
a view field data input step for introducing data of the view field on an eye to be examined by means of a view field measuring means into the apparatus;
a correction step for correcting at least one of said eye fundus image and said eye field measuring data so that said eye fundus image and said view field measuring data are in one-to-one correspondence with each other; and
a compound step for compounding corrected eye fundus image and view field measuring data corrected by said correction means.

7. An ophthalmologic image compound method according to claim 6, wherein:
said correction step corrects at least one of magnification and distortion.

8. An ophthalmologic image compound method according to claim 6, wherein:
said compound step optically compounds said data.

9. An ophthalmologic image compound method according to claim 6, wherein:
said compound step electrically compounds said data.

10. An ophthalmologic image compound method according to claim 6, wherein:
said compound step is performed with a yellow spot of the eye fundus image brought into coincidence with the center of the field of view of the view field measuring data.

11. An ophthalmologic image compound method according to claim 6, wherein:
said compound step is performed with an optic disk of said eye fundus image brought into coincidence with a blind spot of the view field measuring data.

12. An ophthalmologic image compound method according to claim 6, wherein:
said compound step is performed with coordinates of a fixation target of the view field measuring means made to correspond to a position of the fixation target of an eye fundus photographing means.

13. An ophthalmologic image compound method according to claim 6, wherein:
said eye fundus image is a visible eye fundus image photographed under the application of visible light.

14. An ophthalmologic image compound method according to claim 6, further comprising:
a step for producing the eye fundus image with a wide view angle by combining a plurality of eye fundus images.

15. An apparatus for performing an eye field measurement while outputting a corresponding eye fundus image, comprising:
view field measuring means for measuring a view field of an eye to be examined and producing view field measuring data;
eye fundus image input means for introducing an eye fundus image prepared previous to a view field measuring operation;
correction means for correcting at least one of said eye fundus image and said view field measuring data so that said eye fundus image and said view field measuring data correspond to each other in a one-to-one correspondence; and
output means for outputting a corresponding eye fundus image introduced by said eye fundus image input means when the view field measuring operation is being performed.

16 An apparatus for performing an eye field measurement according to claim 15, wherein:
said eye fundus image is a visible eye fundus image photographed under the application of a visible light.

17. An apparatus for performing an eye field measurement according to claim 15, wherein:
said eye fundus image has a wide view angle produced by combining a plurality of eye fundus images.

18. A method for performing an eye field measurement while outputting a corresponding eye fundus image, comprising:
a view field measuring step for measuring a view field of an eye to be examined and producing view field measuring data;
an eye fundus image input step for introducing an eye fundus image prepared previous to a view field measuring operation;
a correction step for correcting at least one of said eye fundus image and said view field measuring data so that said eye fundus image and said view field measuring data correspond to each other in a one-to-one correspondence; and
an output step for outputting a corresponding eye fundus image introduced by said eye fundus image input step when the view field measuring operation is being performed.

19. An ophthalmologic image compound method according to claim 18, wherein:
said correction step corrects at least one of magnification and distortion.

20. An ophthalmologic image compound method according to claim 18 further comprising the step of optically compounding said corrected eye fundus image and said corrected view field measuring data.

21. An ophthalmologic image compound method according to claim 18, further comprising the step of electrically compounding said corrected eye fundus image and said corrected view field measuring data.

22. An ophthalmologic image compound method according to claim 18, further comprising the step of compounding said corrected eye fundus image and said corrected view field measuring data with a yellow spot of the eye fundus image brought into coincidence with center of the field of view of the view field output.

23. An ophthalmologic image compound method according to claim 18, further comprising the step of compounding said corrected eye fundus image and said corrected view field measuring data with an optic disk of said eye fundus image brought into coincidence with a blind spot of the view field output.

24. An ophthalmologic image compound method according to claim 18, further comprising the step of compounding said corrected eye fundus image and said corrected view field measuring data with coordinates of a fixation target of a view field measuring means made to correspond to a position of the fixation target of an eye fundus photographing means.

25. An ophthalmologic image compound method according to claim 18, wherein:
said eye fundus image is a visible eye fundus image photographed under the application of a visible light 26. An ophthalmologic image compound method according to claim 18, wherein:
said eye fundus image has a wide view angle produced by combining a plurality of eye fundus images.

27. An ophthalmologic measuring system, comprising:
eye fundus photographing means for photographing and recording an eye fundus image of an eye to be examined previous to performing a view field measurement;
view field measuring means for measuring a view field of the eye;
output means for outputting said recorded corresponding eye fundus image when the view field measurement is being performed; and
correction and compound means for correcting at least one of said eye fundus image and said view field measuring data so that said eye fundus image and said view field measuring data correspond to each other in a one-to-one correspondence and for compounding the corrected eye fundus image and view field measuring data.

28. An apparatus according to claim 27, wherein:
said eye fundus image is a visible eye fundus image photographed under the application of a visible light.

29. An ophthalmologic measuring method, comprising:
an eye fundus photographing step for photographing and recording an eye fundus image of an eye to be examined previous to performing a view field measurement;
a view field measuring step for measuring a view field of the eye;
an output step for outputting said recorded corresponding eye fundus image when the view field measurement is being performed; and
a correction and compound step for correcting at least one of said eye fundus image and said view field measuring data so that said eye fundus image and said view field measuring data correspond to each other in a one-to-one correspondence and for compounding said corrected eye fundus image and a view field measuring data.

30. An ophthalmologic measuring method according to claim 29, wherein:
said eye fundus image is a visible eye fundus image photographed under the application of a visible light.

31. An ophthalmologic digital image compound method comprising:
an eye fundus image input step for introducing an eye fundus image photographed by an eye fundus photographing means;
an image storing step for storing said introduced eye fundus image in a digital manner;
a view field input step for introducing view field measuring data by means of a view field measuring means;

a correction step for correcting at least one of said digitalized eye fundus image and said view field measuring data so that said stored digital eye fundus image and said view field measuring data correspond to each other in a one-to-one correspondence; and
a compound step for compounding said corrected digital eye fundus image and said view field measuring data in a digital manner.

32. An ophthalmologic digital image compound method according to claim 31, wherein:
said method further comprises a step for storing a plurality of said eye fundus images and for producing a digital eye fundus image having a wide view angle by combining said plurality of eye fundus images.

33. An ophthalmologic digital image compound method according to claim 31, wherein:
said introduced eye fundus image is photographed previous to the view field measurement.

34. An ophthalmologic digital image compound method according to claim 31, wherein:
said correction step corrects at least one of magnification and distortion.

35. An ophthalmologic digital image compound method according to claim 31, wherein:
said compound step is performed with a yellow spot of the eye fundus image brought into coincidence with the center of the field of view of the view field measuring data.

36. An ophthalmologic digital image compound method according to claim 31, wherein:
said compound step is performed with an optic disk of said eye fundus image brought into coincidence with a blind spot of the view field measuring data.

37. An ophthalmologic digital image compound method according to claim 31, wherein:
said compound step is performed with coordinates of a fixation target of a view field measuring means made to correspond to a position of the fixation target of an eye fundus photographing means.

38. An ophthalmologic digital image compound method according to claim 31, wherein:
said eye fundus image is a visible eye fundus image photographed under the application of a visible light.

39. An ophthalmologic image compound apparatus, comprising:
means for introducing a plurality of eye fundus images thereinto;
means for combining said plurality of eye fundus images and making an eye fundus image of a wide angle of view;
view field measuring means for measuring the field of view of an eye to be examined;
means for superposing said eye fundus image of a wide angle of view and an output of said view field measuring means, one upon the other, and compounding said eye fundus image of a wide angle of view and the output of said view field measuring means.

40. An ophthalmologic image compound apparatus according to claim 39, further comprising:
means for correcting the distortion of said introduced eye fundus image.

41. An ophthalmologic image compound apparatus according to claim 39, wherein:
said eye fundus image is a visible image obtained by applying visible light to the eye fundus.

* * * * *

UNITED STATES PATENT AND TRADEMARK OFFICE
CERTIFICATE OF CORRECTION

PATENT NO. : 5,037,194        Page 1 of 2
DATED      : August 6, 1991
INVENTOR(S): Yoshimi Kohayakawa, et al.

It is certified that error appears in the above-identified patent and that said Letters Patent is hereby corrected as shown below:

At [57] ABSTRACT:

Line 4 of the Abstract "measurment" should read --measurement--.

COLUMN 1

Line 50, "view" should read --view;--.

COLUMN 2

Line 8, "the" should be deleted;
    Line 31, "the" should read --of the--.

COLUMN 7

Line 40-41, "of displayed" should read --displayed--.

COLUMN 8

Line 26, "of the" should read --of--;
    Line 28, "and the" should read --and--;
    Line 30, "of the" should read --of--.

COLUMN 9

Line 17, "on" should read --of--.

UNITED STATES PATENT AND TRADEMARK OFFICE
CERTIFICATE OF CORRECTION

PATENT NO. : 5,037,194
DATED : August 6, 1991
INVENTOR(S) : Yoshimi Kohayakawa, et al.

It is certified that error appears in the above-identified patent and that said Letters Patent is hereby corrected as shown below:

COLUMN 11

Line 53, "a" should be deleted.

COLUMN 12

Line 53, "examined;" should read --examined; and--.

Signed and Sealed this

Twenty-third Day of March, 1993

Attest:

STEPHEN G. KUNIN

Attesting Officer     Acting Commissioner of Patents and Trademarks